US012789023B2

(12) United States Patent
Parasmo

(10) Patent No.: US 12,789,023 B2
(45) Date of Patent: Nov. 10, 2026

(54) RADIATION PROTECTIVE GARMENT HAVING A WEIGHT-TRANSFERRING APPARATUS

(71) Applicant: Ronald Jarrod Parasmo, Palm Beach Gardens, FL (US)

(72) Inventor: Ronald Jarrod Parasmo, Palm Beach Gardens, FL (US)

( * ) Notice: Subject to any disclaimer, the term of this patent is extended or adjusted under 35 U.S.C. 154(b) by 0 days.

(21) Appl. No.: 18/812,259

(22) Filed: Aug. 22, 2024

(65) Prior Publication Data

US 2026/0054104 A1 Feb. 26, 2026

(51) Int. Cl.
*A62B 17/00* (2006.01)
*A41D 27/20* (2006.01)
*A61N 5/10* (2006.01)

(52) U.S. Cl.
CPC ............ *A62B 17/006* (2013.01); *A41D 27/20* (2013.01); *A61N 2005/1094* (2013.01)

(58) Field of Classification Search
CPC ............ A61F 5/026; A61N 2005/1094; A62B 17/006; A41D 1/04; A41D 13/01; A41D 27/20; G21F 3/02; G21F 3/03
See application file for complete search history.

(56) References Cited

U.S. PATENT DOCUMENTS 725,903 A * 4/1903 Wilcomb ........... A41D 13/0012 2/94
1,495,489 A * 5/1924 Krause ...................... F41H 1/02 2/2.5
2,156,504 A * 5/1939 Liss ....................... H04R 25/04 381/385
2,304,574 A * 12/1942 Kirschenbaum ... A41D 13/0012 2/94
2,555,871 A * 6/1951 Caggiano ............... G03B 15/03 224/639
3,055,133 A * 9/1962 Anderson ................ A41D 1/04 2/253
3,451,064 A * 6/1969 Dolan .................... A47C 9/025 297/4

(Continued)

FOREIGN PATENT DOCUMENTS

CA 2253050 A1 * 5/2000 ............... G21F 3/02
CN 204087830 U * 1/2015

(Continued)

*Primary Examiner* — Heather Mangine
*Assistant Examiner* — Raquel M. Weis
(74) *Attorney, Agent, or Firm* — Simpson & Simpson, PLLC

(57) ABSTRACT

A radiation protective garment, or a garment, having a front surface, a back surface, a waist portion and a shoulder portion, said garment to be worn by a person having a waist and shoulders, comprising, a first upper pocket arranged proximate the back surface and the shoulder portion, a second upper pocket arranged proximate the back surface and the shoulder portion, a first lower pocket arranged on the back surface and proximate the waist portion, a second lower pocket arranged on the back surface and proximate the waist portion, a first plurality of flexible rods supported by the first upper pocket and the first lower pocket, and a second plurality of flexible rods supported by the second upper pocket and the second lower pocket.

19 Claims, 9 Drawing Sheets

(56) References Cited

U.S. PATENT DOCUMENTS

| | | | | | |
|---|---|---|---|---|---|
| 4,328,533 | A * | 5/1982 | Paredes | A41D 13/01 | 362/108 |
| 4,417,146 | A * | 11/1983 | Herbert | G21F 3/03 | 250/516.1 |
| 4,422,719 | A * | 12/1983 | Orcutt | G02B 6/02033 | 362/582 |
| D273,818 | S * | 5/1984 | Spencer | D3/227 | |
| 4,467,476 | A * | 8/1984 | Herbert | G21F 3/03 | 2/2.5 |
| 4,539,700 | A * | 9/1985 | Sato | H04R 5/023 | 455/343.1 |
| 4,637,075 | A * | 1/1987 | Ingrisano | A61F 17/00 | 2/253 |
| 4,637,076 | A * | 1/1987 | Tartt | A41D 15/04 | 2/102 |
| 4,669,127 | A * | 6/1987 | Swanson | A41D 13/0012 | 2/46 |
| 4,876,724 | A * | 10/1989 | Suzuki | H05K 11/00 | 381/301 |
| 4,924,362 | A * | 5/1990 | Janko | H05K 1/038 | 362/240 |
| 5,070,436 | A * | 12/1991 | Alexander | G08B 5/004 | 362/108 |
| 5,249,106 | A * | 9/1993 | Barnes | A41D 13/01 | 362/108 |
| 5,424,922 | A * | 6/1995 | Wise | A41D 13/01 | 362/108 |
| 5,515,543 | A * | 5/1996 | Gioello | A41D 31/102 | 2/DIG. 1 |
| 5,555,490 | A * | 9/1996 | Carroll | G06F 1/163 | 2/905 |
| 5,671,480 | A * | 9/1997 | Krout | A41D 13/0125 | 441/89 |
| 5,722,573 | A * | 3/1998 | Carnel | A45F 3/16 | 224/148.2 |
| 5,803,667 | A * | 9/1998 | Seligman | B63C 11/30 | 405/185 |
| 5,834,789 | A * | 11/1998 | Marchione | G21F 3/02 | 250/516.1 |
| 5,844,246 | A * | 12/1998 | Marchione | G21F 3/02 | 250/516.1 |
| 6,085,698 | A * | 7/2000 | Klein | A41D 13/01 | 119/859 |
| 6,106,130 | A * | 8/2000 | Harding | G08B 5/004 | 362/108 |
| 6,185,738 | B1 * | 2/2001 | Sidebottom | F41H 1/02 | 2/2.5 |
| 6,267,482 | B1 * | 7/2001 | Miller | G02B 6/0053 | 362/108 |
| 6,405,378 | B1 * | 6/2002 | Garner | A41D 15/04 | 2/102 |
| 6,449,770 | B1 * | 9/2002 | Taylor | A41D 13/0007 | 128/869 |
| 6,478,510 | B1 * | 11/2002 | Young | B63C 11/08 | 441/106 |
| 6,517,214 | B1 * | 2/2003 | Mitchell, Jr. | A41D 13/01 | 362/240 |
| 6,991,343 | B2 * | 1/2006 | Langley | A41D 13/0518 | 362/108 |
| 6,997,573 | B2 * | 2/2006 | Maese | A41D 13/01 | 362/108 |
| 7,281,813 | B2 * | 10/2007 | Golle | A41D 13/01 | 362/108 |
| 7,440,581 | B2 * | 10/2008 | Wiener | H04R 5/023 | 381/301 |
| 7,549,179 | B1 * | 6/2009 | Saied | A41D 13/0012 | 2/114 |
| 7,865,975 | B2 * | 1/2011 | Davies | A61F 5/026 | 2/310 |
| 8,067,759 | B1 * | 11/2011 | Swartz | G21F 3/02 | 2/92 |
| 8,353,065 | B1 * | 1/2013 | Crye | F41H 1/02 | 2/2.5 |
| 8,598,554 | B2 * | 12/2013 | Rees | G21F 3/02 | 250/516.1 |
| 8,710,477 | B1 * | 4/2014 | Marchione | A41D 13/0025 | 2/457 |
| 8,756,718 | B2 * | 6/2014 | Tymofy | A41D 31/14 | 2/256 |
| 8,997,262 | B2 * | 4/2015 | Klein | A45F 3/08 | 2/2.5 |
| 9,185,964 | B2 * | 11/2015 | Crye | A45F 3/047 | |
| RE46,069 | E * | 7/2016 | GibsonHorn | A63B 21/4005 | |
| 9,603,393 | B2 | 3/2017 | Crye | | |
| 9,629,443 | B2 * | 4/2017 | Searle | A45F 3/10 | |
| 9,746,165 | B2 * | 8/2017 | Ritter | F21V 21/145 | |
| 9,999,290 | B2 * | 6/2018 | Klein | A45F 3/08 | |
| 10,165,847 | B2 * | 1/2019 | Chapman | A45F 3/10 | |
| 10,786,054 | B1 * | 9/2020 | Rosado | A45B 11/02 | |
| 10,856,588 | B2 * | 12/2020 | Ward | A41D 13/0012 | |
| 11,200,993 | B2 * | 12/2021 | Gerges | A61B 6/107 | |
| 11,202,479 | B2 * | 12/2021 | Collins | A45F 3/14 | |
| 2002/0152533 | A1 * | 10/2002 | Lesley | A41D 13/01 | 2/102 |
| 2003/0196243 | A1 * | 10/2003 | Tadros | A45F 4/00 | 2/89 |
| 2004/0114350 | A1 * | 6/2004 | Golle | A41D 1/04 | 362/108 |
| 2004/0117890 | A1 * | 6/2004 | Golle | A41D 1/04 | 2/102 |
| 2005/0045687 | A1 * | 3/2005 | Willows | A41D 13/01 | 224/637 |
| 2006/0242799 | A1 * | 11/2006 | Flossner | A41D 13/0012 | 24/3.7 |
| 2007/0012261 | A1 * | 1/2007 | Altieri | A01K 1/029 | 119/770 |
| 2007/0074327 | A1 * | 4/2007 | Davies | A61F 5/026 | 2/44 |
| 2007/0105404 | A1 * | 5/2007 | Lee | H01R 12/592 | 439/37 |
| 2008/0047046 | A1 * | 2/2008 | Maier | A41D 1/04 | 2/102 |
| 2008/0188785 | A1 * | 8/2008 | Shutes | A41D 13/05 | 2/467 |
| 2008/0201818 | A1 * | 8/2008 | Nilforushan | A61F 7/02 | 607/114 |
| 2008/0301863 | A1 * | 12/2008 | Goff | A41D 13/0012 | 2/467 |
| 2010/0144490 | A1 * | 6/2010 | Purdy | A63B 21/4007 | 2/69 |
| 2010/0319102 | A1 * | 12/2010 | Kemper | A41D 13/1209 | 2/114 |
| 2011/0038142 | A1 * | 2/2011 | Ritter | F21V 21/145 | 362/108 |
| 2011/0043755 | A1 * | 2/2011 | Gibson-Horn | A61F 5/028 | 351/203 |
| 2011/0055992 | A1 * | 3/2011 | Roux | F41H 1/02 | 2/2.5 |
| 2012/0233749 | A1 * | 9/2012 | Tymofy | A41D 31/14 | 2/463 |
| 2013/0091624 | A1 * | 4/2013 | Czajka | A41D 13/1209 | 2/456 |
| 2013/0094189 | A1 * | 4/2013 | Kimitri | A41D 13/01 | 362/108 |
| 2014/0022766 | A1 * | 1/2014 | Wright | G08B 5/004 | 362/108 |
| 2014/0245529 | A1 * | 9/2014 | Beckman | A41D 13/0531 | 2/455 |
| 2014/0361058 | A1 * | 12/2014 | Gill | A45F 3/047 | 224/259 |
| 2015/0004131 | A1 * | 1/2015 | Milstein | A61P 39/00 | 250/516.1 |
| 2015/0200045 | A1 * | 7/2015 | Mathieu | A45F 5/02 | 335/286 |
| 2016/0050995 | A1 * | 2/2016 | Bentley | A41D 27/207 | 2/114 |

(56) References Cited

U.S. PATENT DOCUMENTS

| | | | | |
|---|---|---|---|---|
| 2016/0069647 | A1* | 3/2016 | Crye | A45F 3/047 2/102 |
| 2017/0095063 | A1* | 4/2017 | Rowell | A45F 3/14 |
| 2018/0140078 | A1* | 5/2018 | Williamson | A41D 1/002 |
| 2018/0161617 | A1* | 6/2018 | Rao | A41D 31/00 |
| 2018/0228235 | A1* | 8/2018 | Truelove, III | A41F 19/00 |
| 2019/0080810 | A1* | 3/2019 | Arvin | G21F 1/12 |
| 2019/0304613 | A1* | 10/2019 | Gerges | G21F 3/02 |
| 2020/0068964 | A1* | 3/2020 | Brandt | A41D 27/20 |
| 2020/0155264 | A1 | 5/2020 | Waterman et al. | |
| 2020/0178678 | A1* | 6/2020 | Collins | A45F 3/14 |
| 2020/0305581 | A1* | 10/2020 | Barklow | A41D 13/0007 |
| 2020/0353891 | A1* | 11/2020 | Turjeman | B60R 22/30 |
| 2021/0378331 | A1* | 12/2021 | Kassab | A45F 3/10 |
| 2022/0142803 | A1* | 5/2022 | Ochoa | A61F 5/026 |
| 2023/0030890 | A1* | 2/2023 | Baggen | F41H 1/02 |
| 2023/0117365 | A1* | 4/2023 | North | A61B 5/346 600/301 |
| 2023/0320437 | A1* | 10/2023 | Lemerick | A63B 21/0555 2/244 |
| 2023/0320883 | A1* | 10/2023 | Ross | A41B 1/00 602/69 |
| 2023/0389677 | A1* | 12/2023 | Flohr | A61B 6/107 |
| 2024/0041189 | A1* | 2/2024 | Schwager | A45F 3/047 |
| 2024/0276964 | A1* | 8/2024 | Drinkard | A45F 3/04 |
| 2026/0054104 | A1* | 2/2026 | Parasmo | A41D 27/20 |

FOREIGN PATENT DOCUMENTS

| | | | | | |
|---|---|---|---|---|---|
| CN | 218999596 | U | * | 5/2023 | |
| EP | 2488131 | B1 | * | 11/2015 | A61F 5/05841 |
| GB | 2462477 | A | * | 2/2010 | A63B 21/0602 |
| RU | 136299 | U1 | * | 1/2014 | |
| RU | 2516842 | C2 | * | 5/2014 | |
| RU | 2640991 | C1 | * | 1/2018 | |

* cited by examiner

RADIATION PROTECTIVE GARMENT HAVING A WEIGHT-TRANSFERRING APPARATUS

FIELD

The present invention relates to an x-ray apron having a weight-transfer apparatus and generally, the present invention may relate to a weight-transfer apparatus for heavy and/or weighted articles of clothing.

BACKGROUND

Radiation shielding materials are used for a variety of radiologic applications, such as X-rays. The use of radiation in diagnosing and treating patients has significantly advanced the field of medicine and saved or extended countless lives. Advances in technology and more sophisticated applications have improved standard treatments for the benefit of the patient. Radiation use does, however, come with risks. Those who use radiation, radiologists, doctors, etc., must be adequately trained in radiation safety, radiation physics, the biologic effects of radiation, and injury prevention to ensure patient safety. One major principle of mitigating external radiation exposure is shielding. Shielding means using absorber material, such as Plexiglas for beta particles and lead for X-rays and gamma rays, to reduce radiation exposure.

There are three predominant radiation shielding materials, lead (Pb), lead composites (a combination of lead and other lighter weight metals or materials, e.g., tin, rubber, PVC vinyl, etc.), and non-lead or lead free (e.g., tin (Sn), antimony (Sb), tungsten (W) bismuth (Bi) or other elements). Typically, medical professionals who may exposed to radiation, use “x-ray aprons”, which are articles of clothing having one of the three aforementioned shielding materials inserted into, or woven into, or a combination thereof.

X-ray aprons can come in a variety of clothing designs, such as an apron style having only a frontal covering or a rear and a frontal covering, vests, long sleeves, etc. If shielding material is added to a traditional article of clothing, any apparel can become an X-ray apron.

Of the three general types of radiation shielding material, lead is the most commonly used in x-ray aprons, and also the heaviest. Although a lead composition x-ray apron can be approximately 25% lighter than an entirely lead x-ray apron, and non-lead, or lead free x-ray aprons can be approximately 40% lighter than an entirely lead x-ray apron, x-ray aprons are still much heavier than typical clothing.

The additional weight of an x-ray apron, in combination with extended wear of the x-ray apron, i.e., four to five days a week for at least seven hours, can create a plurality of problems for the medical provides, e.g., back pain and/or soreness, poor or degraded posture, increased fatigue, etc.

Thus, there is a long-felt need for a radiation protective garment having at least one weight transferring apparatus, specifically, at least one weight transferring apparatus arranged to transfer a weight of the radiation protective garment, or other weighted garment, from shoulders of a user to proximate a waist of the user, or hips of the user.

SUMMARY

Generally, the present invention comprises a radiation protective garment having a front surface, a back surface, a waist portion and a shoulder portion, said protective garment to be worn by a person having a waist and shoulders, comprising, a first upper pocket arranged proximate the back surface and the shoulder portion, a second upper pocket arranged proximate the back surface and the shoulder portion, a first lower pocket arranged on the back surface and proximate the waist portion, a second lower pocket arranged on the back surface and proximate the waist portion, a first plurality of flexible rods supported by the first upper pocket and the first lower pocket, and a second plurality of flexible rods supported by the second upper pocket and the second lower pocket.

In some arrangements, the radiation protective garment may further comprise a third lower pocket arranged between the first and second lower pockets on the back surface.

In other configurations, the first plurality of flexible rods and the second plurality of flexible rods of the radiation protective garment each comprise four flexible rods.

In further aspects, each of said flexible rods of the first and second plurality of flexible rods of the radiation protective garment are comprised of fiberglass.

In other embodiments, The first and second lower pockets of radiation protective garment are arranged substantially proximate a center line of the back surface.

In some configurations, the first plurality of flexible rods of the radiation protective garment have a first flex point when supported by the first upper pocket and the first lower pocket; and, the second plurality of flexible rods of the radiation protective garment have a second flex point when support by the second upper pocket and the second lower pocket.

In other arrangements, when the radiation protective garment is worn by the person, the shoulder portion is substantially elevated above the shoulders of the person when the first plurality of flexible rods are supported by the first upper pocket and the first lower pocket; and, the second plurality of flexible rods are supported by the second upper pocket and the second lower pocket.

In some embodiments, the aforementioned garment may further include a belt secured proximate the waist portion on the rear surface.

It should be noted that the present invention may be used in conjunction with other weighted garments. As such, the present invention could also comprise a garment having a front surface, a back surface, a waist portion and a shoulder portion, the garment to be worn by a person having a waist and shoulders, further comprising: a first upper pocket arranged proximate the back surface and the shoulder portion; a second upper pocket arranged proximate the back surface and the shoulder portion; a first lower pocket arranged on the back surface and proximate the waist portion; a second lower pocket arranged on the back surface and proximate the waist portion; a first at least one flexible rod removably arranged within the first upper pocket and the first lower pocket; and, a second at least one flexible rod removably arranged within the second upper pocket and the second lower pocket, wherein when the rods are seated within the respective pockets they are flexed and extend away from the back surface.

The aforementioned garment may further comprise a support belt secured proximate the waist portion on the back surface, the belt comprising a first section and a section adapted to be removably secured proximate the front surface, adapted to afford a selectable circumference of the joined first and second sections, thereby allowing a selective about of compression to be imparted by the first and second sections on the waist portion.

In some embodiments, the first at least one flexible rod of the aforementioned garment may comprise a first plurality of flexible rods; and, the second at least one flexible rod of the aforementioned garment may comprise a second plurality of flexible rods.

In another possible embodiment, the first plurality of flexible rods of the aforementioned garment may comprise at least four flexible rods; and, the second plurality of flexible rods of the aforementioned garment may comprise at least four flexible rods.

These and other objects, features, and advantages of the present invention will become readily apparent upon a review of the following detailed description of the invention, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which:

FIGS. 2A and 2B are enlarged portions of the invention shown in FIG. 2;

DETAILED DESCRIPTION

Figure 1:
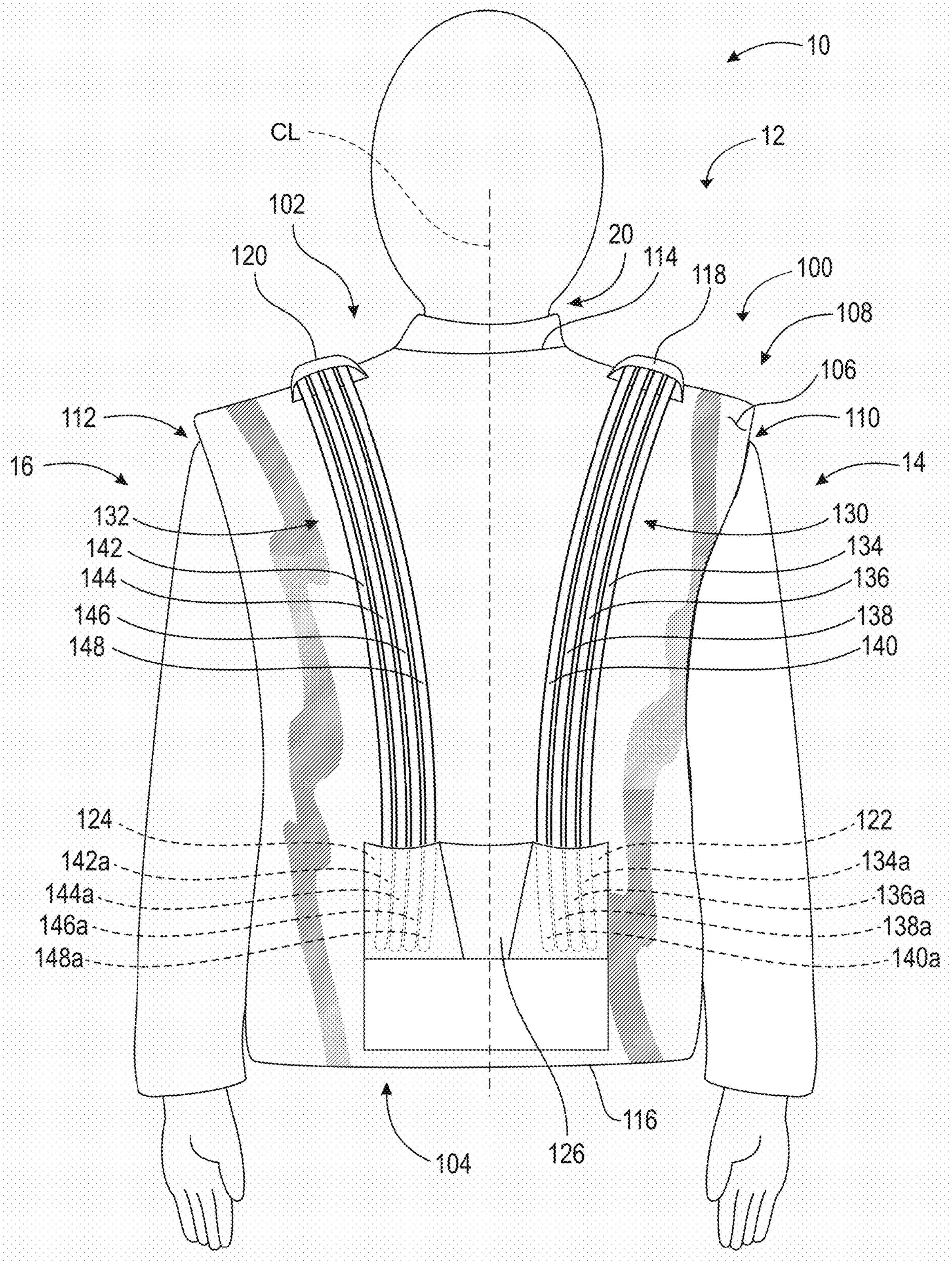
FIG. 1 is a rear view of the present invention being worn.

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims. Those in the art will understand that any suitable material, now known, or hereafter developed, may be used in forming the present invention described herein.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments.

Those in the art will understand that any suitable material, now known or hereafter developed, may be used in forming the present invention described herein.

It should be noted that the terms “including”, “includes”, “having”, “has”, “contains”, and/or “containing”, should be interpreted as being substantially synonymous with the terms “comprising” and/or “comprises”.

It should be appreciated that the term “substantially” is synonymous with terms such as “nearly,” “very nearly,” “about,” “approximately,” “around,” “bordering on,” “close to,” “essentially,” “in the neighborhood of,” “in the vicinity of,” etc., and such terms may be used interchangeably as appearing in the specification and claims. It should be appreciated that the term “proximate” is synonymous with terms such as “nearby,” “close,” “adjacent,” “neighboring,” “immediate,” “adjoining,” etc., and such terms may be used interchangeably as appearing in the specification and claims. The term “approximately” is intended to mean values within ten percent of the specified value.

The word “example” or “exemplary” is used herein to mean “serving as an example, instance, or illustration.” Any implementation described herein as “exemplary” is not necessarily to be construed as preferred or advantageous over other implementations.

If the specification states a component or feature “may,” “can,” “could,” “should,” “would,” “preferably,” “possibly,” “typically,” “optionally,” “for example,” “often,” or “might” (or other such language) be included or have a characteristic, that a specific component or feature is not required to be included or to have the characteristic. Such a component or feature may be optionally included in some embodiments, or it may be excluded.

It should be understood that use of “or” in the present application is with respect to a “non-exclusive” arrangement, unless stated otherwise. For example, when saying that “item x is A or B,” it is understood that this can mean one of the following: (1) item x is only one or the other of A and B; (2) item x is both A and B. Alternately stated, the word “or” is not used to define an “exclusive or” arrangement. For example, an “exclusive or” arrangement for the statement “item x is A or B” would require that x can be only one of A and B. Furthermore, as used herein, “and/or” is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

Moreover, as used herein, the phrases “comprises at least one of” and “comprising at least one of” in combination with a system or element is intended to mean that the system or element includes one or more of the elements listed after the phrase. For example, a device comprising at least one of: a first element; a second element; and, a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element. A similar interpretation is intended when the phrase "used in at least one of:" is used herein. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element. A similar interpretation is intended when the phrase "used in at least one of:" or "one of:" is used herein.

Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

The terms "distal" or "distally" are intended to be exemplary directional terms and should be interpreted to mean that a first component is arranged away from a second component. Likewise, the terms "proximal" or "proximally" are intended to be exemplary directional terms and should be interpreted to mean that a first component is arranged close to a second component.

Adverting now to the figures, the following description should be taken in view of FIGS. 1 and 2, which respectively illustrate a front and rear view of person 10 wearing radiation protective garment with weight transferring apparatus 100 (hereinafter "garment"). Generally, garment 100 includes neck end 102, waist end 104, back side 106, front side 108, first end 108*a*, and second end 108*b*. Neck/head hole 114 is disposed proximate neck end, waist hole 116 is arranged at waist end, first arm hole 110 is disposed proximate neck end and distally in relation to neck/head hole 114, and second arm hole 112 is disposed proximate neck end, distally in relation to neck/head hole 114, and opposite first arm hole 110. As shown, person 100 has neck 20 arranged within neck/head hole, arm 14 through first arm hole 110, arm 16 through second arm hole 112, shoulder 22 arranged at least partially within first arm hole 110, shoulder 24 arranged at least partially within second arm hole 112, and waist 18 (shown in FIG. 3) through waist hole 116. As such, garment 100 substantially covers the entirety of a torso of person 100 (i.e., the torso is under garment 100).

Garment 100 includes a weight transferring apparatus comprising first upper pocket 118, second upper pocket 120, first lower pocket 122, second lower pocket 124, first plurality of flexible rods 130, and second plurality of flexible rods 132. First upper pocket 118 is disposed above shoulder 22, proximate back side 106 and neck end 102. Second upper pocket 120 is disposed above shoulder 24, proximate back side 106 and neck end 102, and oppositely arranged in relation to first upper pocket 118. First lower pocket 122 is disposed on back side 106 proximate waist end 104 and arm 14, and second lower pocket 124 is disposed on back side 106 proximate waist end 104 and arm 16. In a preferred embodiment, first lower pocket 122 is a mirror image of second lower pocket 124 taken generally along center line CL of garment 100. To apply a weight transferring effect, first plurality of flexible rods 130 are contained within first upper pocket 118 and first lower pocket 122, and second plurality of flexible rods 132 are contained within second upper pocket 120 and second lower pocket 124.

In a preferred embodiment, first plurality of flexible rods 130 comprises first flexible rod 134, second flexible rod 136, third flexible rod 138, and fourth flexible rod 140. First flexible rod 134 includes first end 134*a* and second end 134*b*. Second flexible rod 136 includes first end 136*a* and second end 136*b*. Third flexible rod 138 includes first end 138*a* and second end 138*b*. Fourth flexible rod 140 includes first end 140*a* and second end 140*b*. In a preferred embodiment, second plurality of flexible rods 132 comprises fifth flexible rod 142, sixth flexible rod 144, seventh flexible rod 146, and eighth flexible rod 148. Fifth flexible rod 142 includes first end 142*a* and second end 142*b*. Sixth flexible rod 144 includes first end 144*a* and second end 144*b*. Seventh flexible rod 146 includes first end 146*a* and second end 146*b*. Eighth flexible rod 148 includes first end 148*a* and second end 148*b*.

Figure 2:
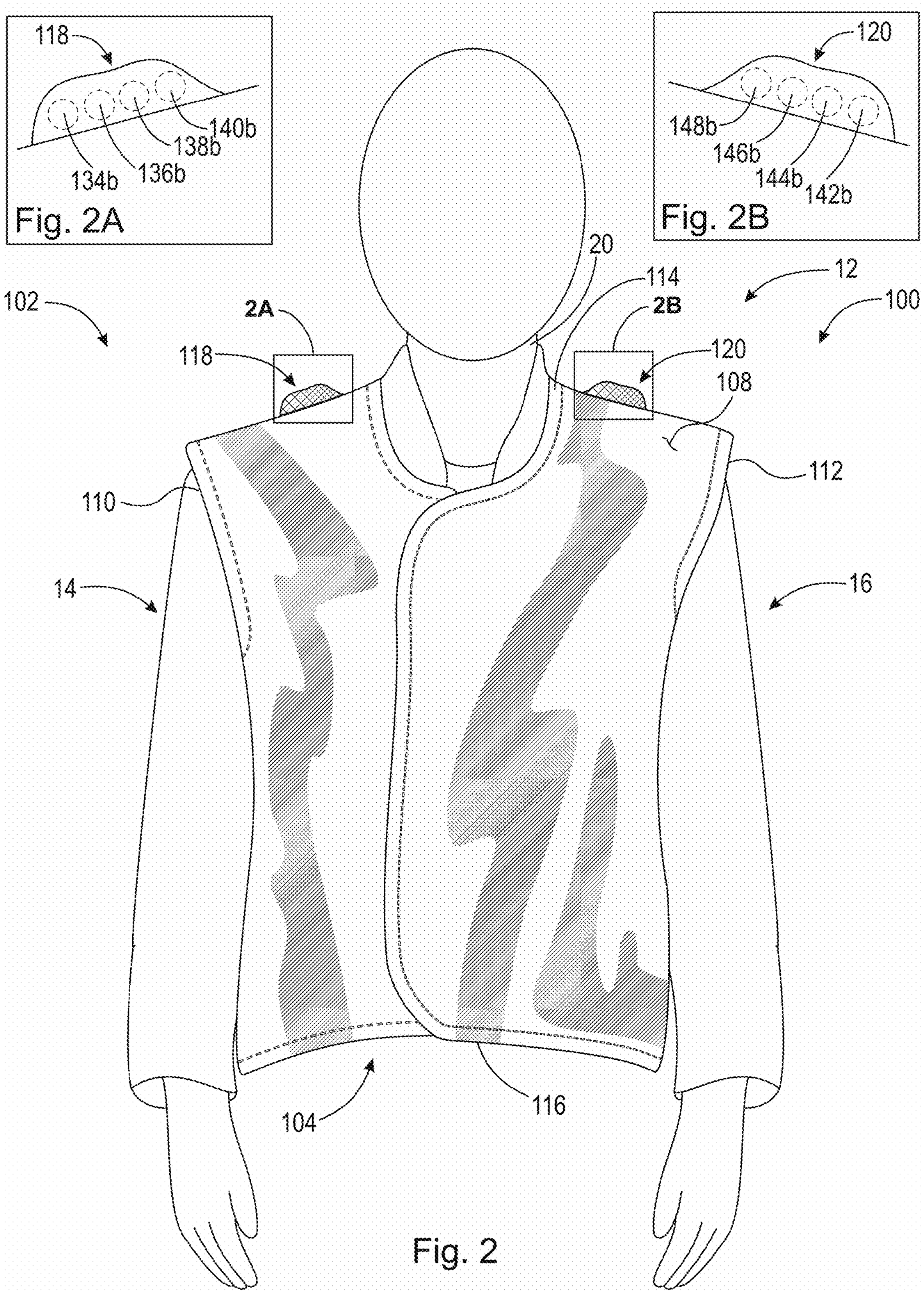
FIG. 2 is a front view of the invention shown in FIG. 1.

As illustrated in FIG. 1, first ends 134*a*-140*a* of flexible rods 134-140 are arranged to be inserted within first lower pocket 122 and first ends 142*a*-148*a* of flexible rods 142-148 are arranged to be inserted within second lower pocket 124. As illustrated in FIG. 2, specifically in FIGS. 2A and 2B, second ends 134*b*-140*b* of flexible rods 134-140 are arranged to be inserted within first upper pocket 118 and second ends 142*b*-148*b* of flexible rods 142-148 are arranged to be inserted within second upper pocket 120.

Figure 3:
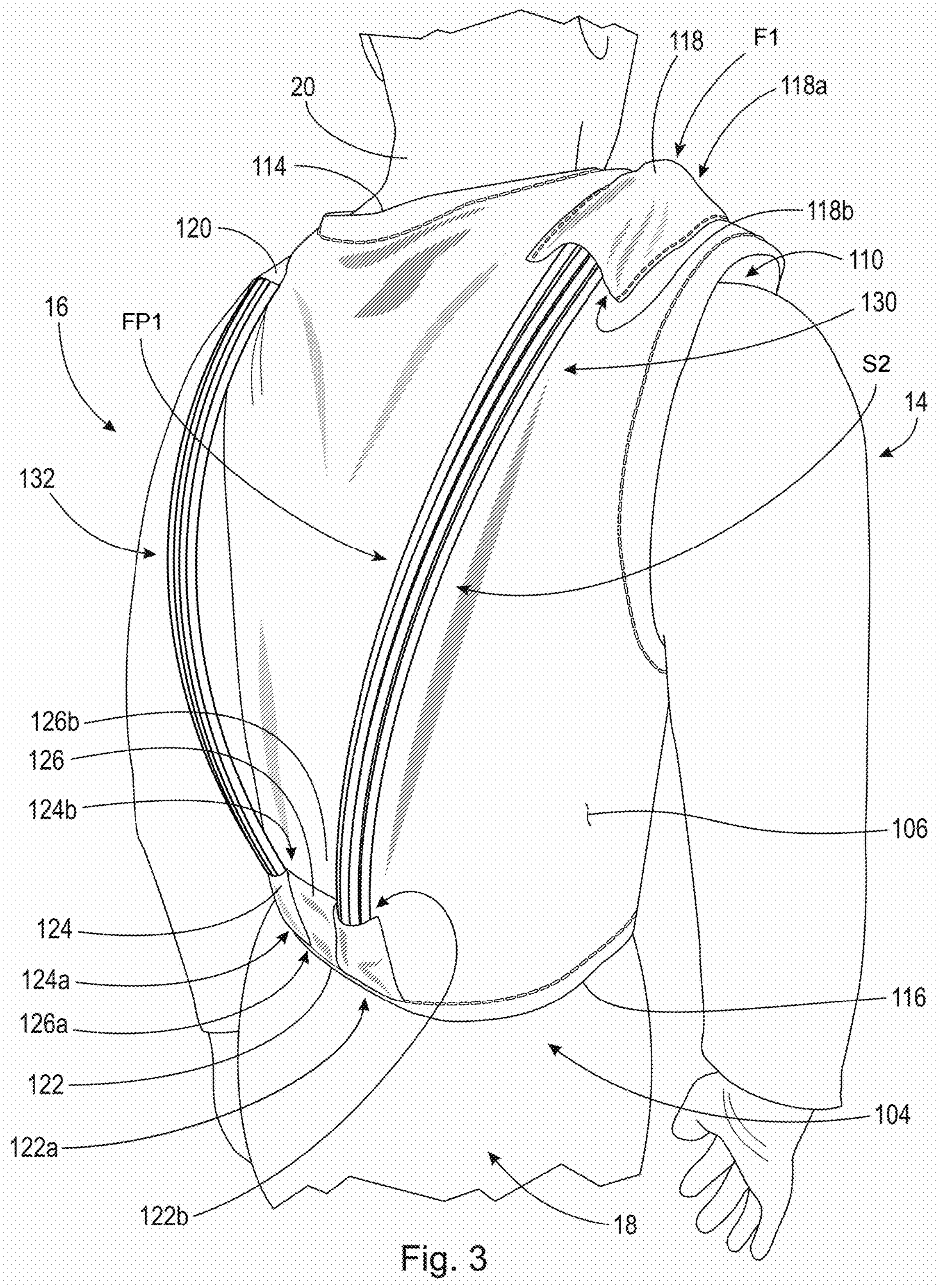
FIG. 3 is a rear-right perspective view of the invention shown in FIG. 1.

As generally shown in FIG. 3, first plurality of flexible rods 130, when each of the respective ends are inserted and substantially supported by first upper pocket 118 and first lower pocket 122, flex point FP1 is created on each of first plurality of flexible rods 130, thereby imparting force at force point F1 on first upper pocket 118 from the second ends of first plurality of flexible rods 130. This force, from bending first plurality of flexible rods 130, lifts a portion of garment 100 between arm hole 110 and neck hole 114 creating space S1.

Figure 4:
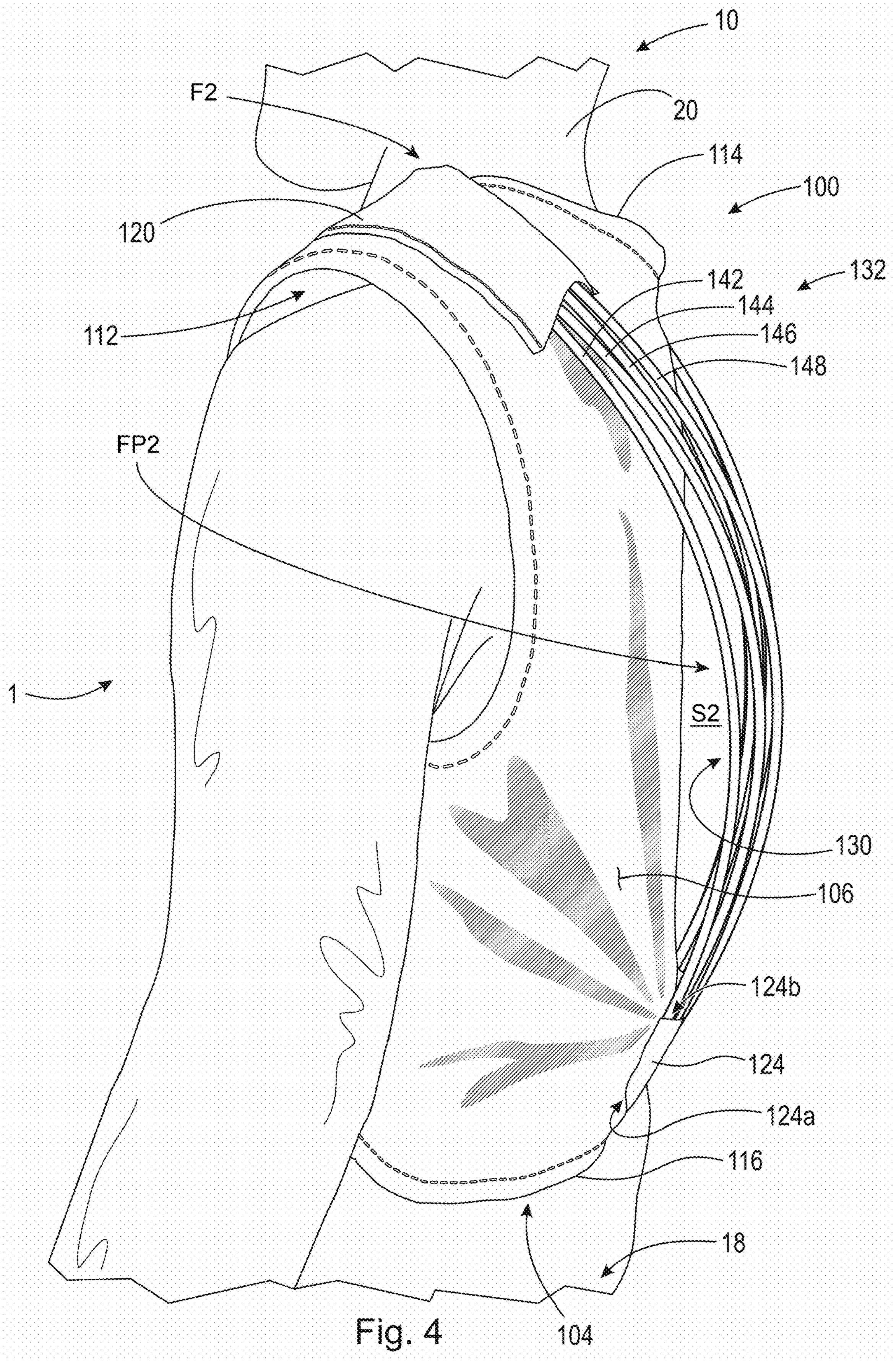
FIG. 4 is a rear-left perspective view of the invention shown in FIG. 1.

As generally shown in FIG. 4, second plurality of flexible rods 132, when each of the respective ends are inserted and substantially supported by second upper pocket 120 and first lower pocket 124, flex point FP2 is created on each of second plurality of flexible rods 132, thereby imparting force at force point F2 on second upper pocket 120 from the second ends of second plurality of flexible rods 132. This force, from bending second plurality of flexible rods 132, lifts a portion of garment 100 between arm hole 112 and neck hole 114 creating space S2.

Figure 5:
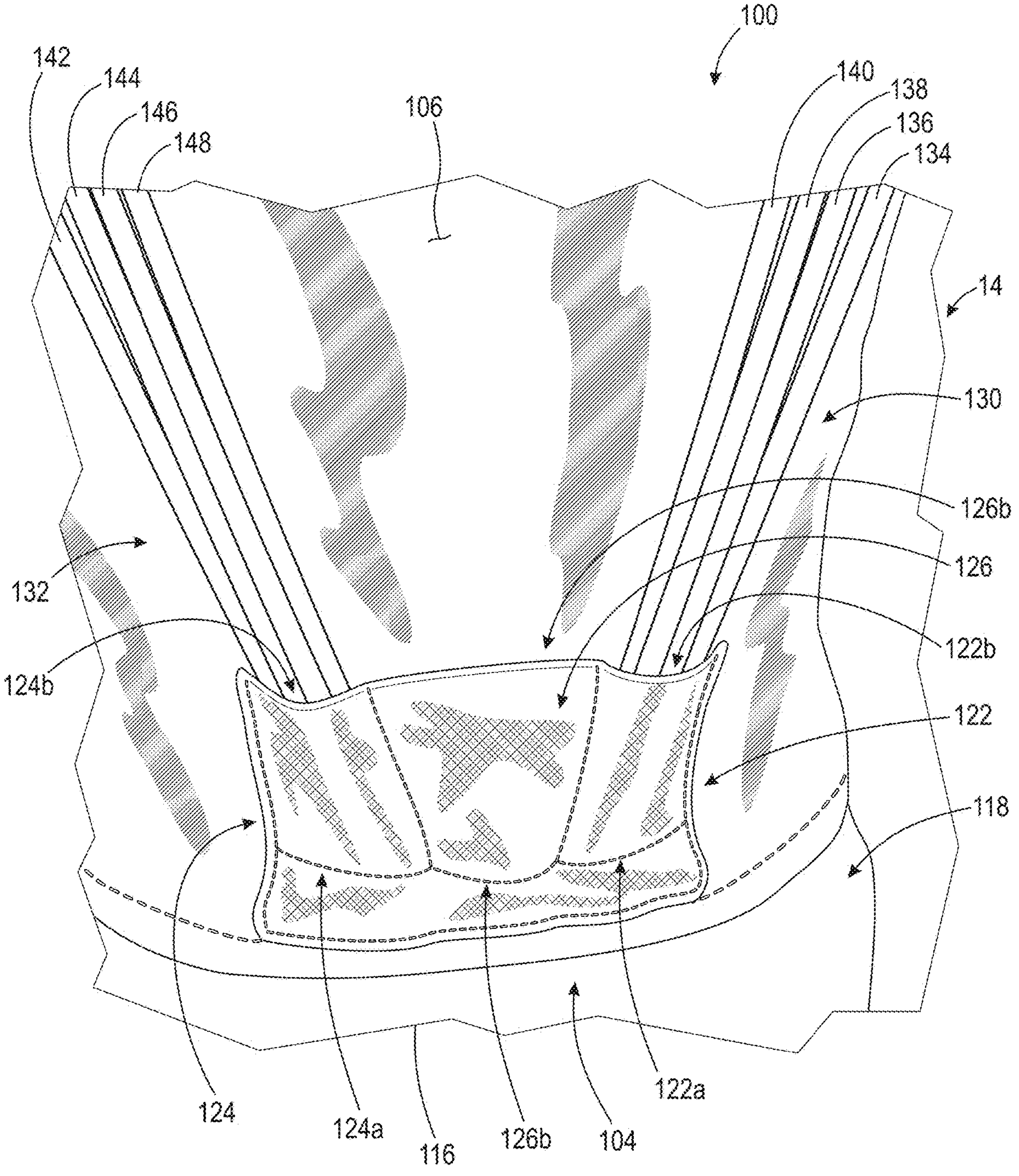
FIG. 5 is an enlarged rear view of the invention shown in FIG. 1.

The illustrations in FIGS. 4 and 5, generally illustrate how pluralities of rods 130 and 132 remove weight from the shoulders 22 and 24 of person 10 wearing garment 100 and shift that weight, via flexible rods 134-148, towards waist 18, generally illustrated by garment 100 being lifted off of shoulders 22 and 24 of person 10 and spaces S1 and S2 being created. This weight-transferring or weight-shifting action of garment 100 is afforded by each of flexible rods 134-148 having a substantially longitudinal "resting" position, i.e., straight up and down. When force is imparted on flexible rods 134-148, i.e., bending and creating flex points FP1 and FP2 (See FIGS. 3 and 4), e.g., when flexible rods 134-148 are inserted into pockets 118-124, flexible rods 134-148 are arranged to resist the bending, thereby pushing garment 100 up and off of shoulders 22 and 24 of person 100, creating spaces S1 and S2 between shoulders 22 and 24 and garment 100 (See FIGS. 3 and 4).

In a preferred embodiment, each of rods 134-148 are comprised of a fiberglass, or alternatively, a semi-flexible polymer, semi-flexible plastic, semi-flexible plastic/polymer combination, carbon fiber, metals, metal/plastic combinations, etc. It should be appreciated however, that those in the art will understand that any suitable material, now known or hereafter developed, may be used in forming flexible rods 134-148.

Figure 6:
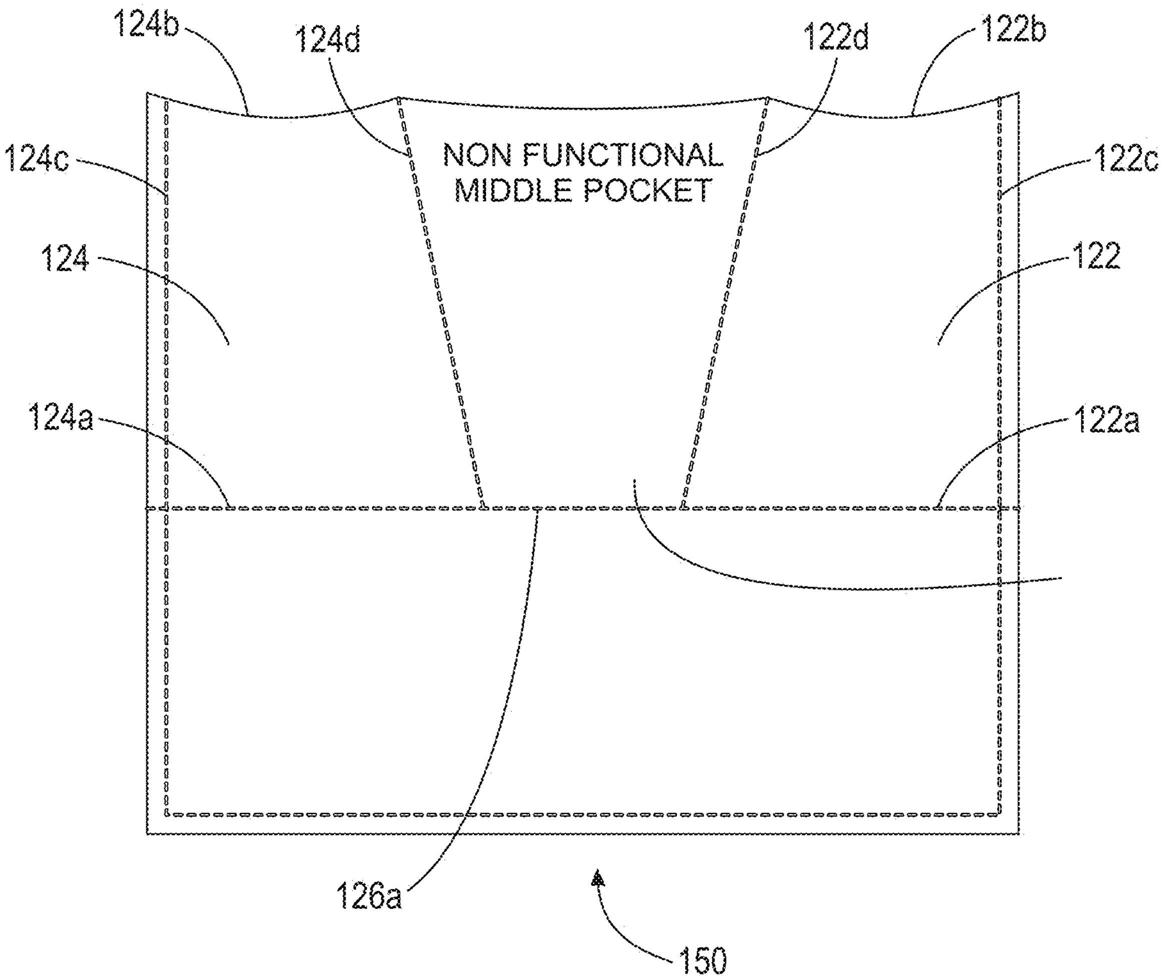
FIG. 6 is an enlarged view of lower pockets of the invention shown in FIG. 1.

FIG. 6 generally illustrates an enlarged view of a lower pocket assembly of garment 100. In some embodiments, garment 100 includes lower pocket assembly 150. Lower pocket assembly 150 comprises at least one of first lower pocket 122, second lower pocket 124, third lower pocket 126, and lower section 152. First lower pocket 122 includes closed end 122*a*, open end 122*b*, first closed side end 122*c*, and second closed side end 122*d*, thereby forming an internal compartment having an opening thereto. Second lower pocket 124 includes closed end 124*a*, open end 124*b*, first closed side end 124*c*, and second closed side end 124*d*, thereby forming an internal compartment having an opening thereto. Third lower pocket 126 is formed by closed end 126*a*, open end 126*b*, second closed side end 122*d*, and second closed side end 124*d*, thereby forming an internal compartment having an opening thereto. It should be noted that closed ends 122*a*, 124*a*, and 126*a*, first closed side ends 122*c* and 124*c*, and second closed side ends 122*d* and 124*d*, may be stitched seams from lower pocket assembly 150 onto back side 106 of garment 100 (See FIG. 1). Alternatively, lower pocket assembly 150 may be fixedly secured to back side 106 of garment 100 in a variety of ways, e.g., hot meld, and the like, so long as lower pocket assembly 150 is fixedly secured to garment 100.

Figure 7:
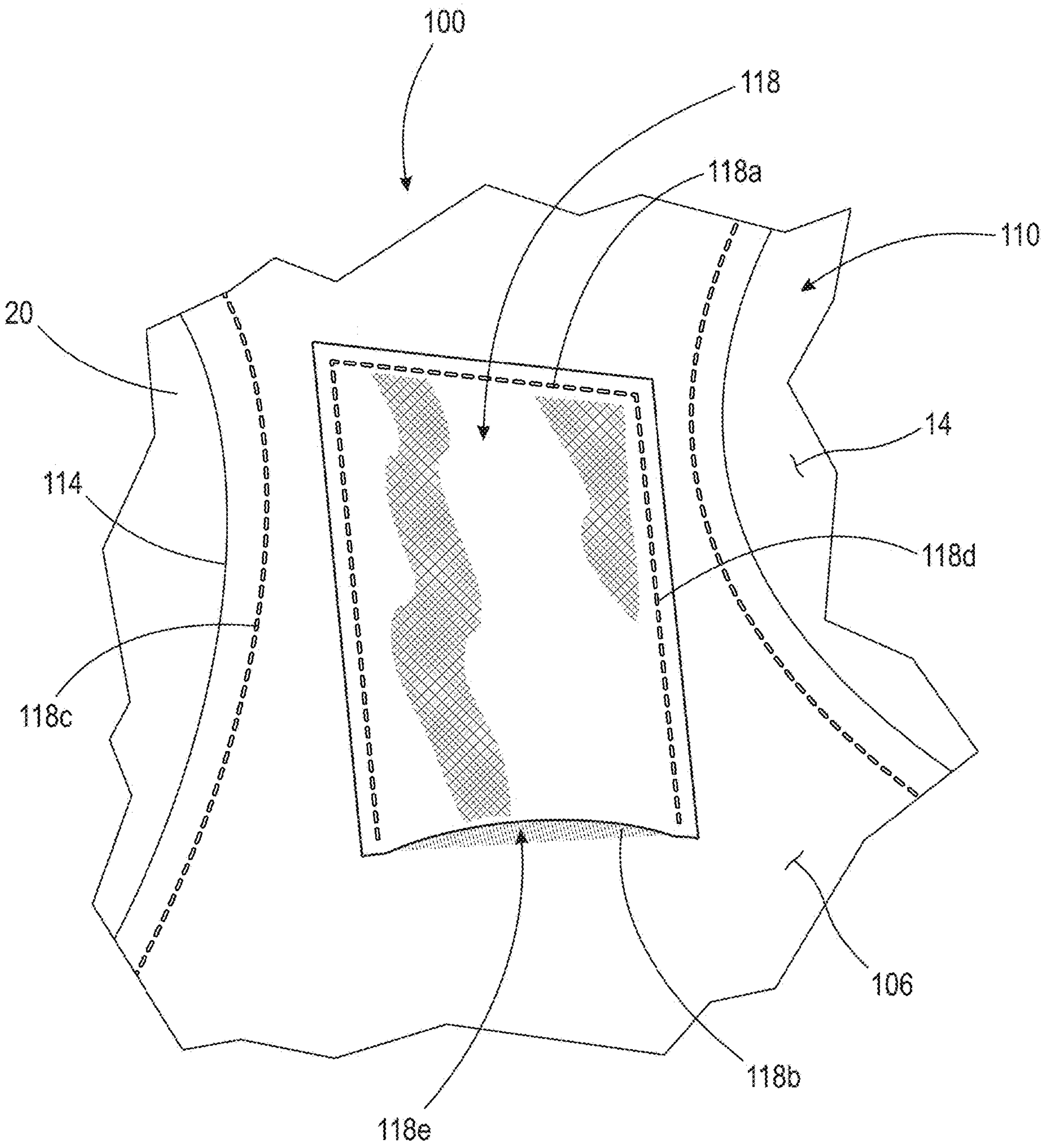
FIG. 7 is an enlarged view of an upper pocket of the invention shown in FIG. 1.

FIG. 7 generally illustrates an enlarged view of an upper pocket assembly of garment 100, specifically, first upper pocket 118. It should be noted that the following description also applies to second upper pocket 120 (See FIG. 1). In some arrangements, first upper pocket 118 includes closed end 118*a*, open end 118*b*, first closed side end 118*c*, and second closed side end 118*d*, thereby forming internal compartment 118*e* having an opening thereto. It should be noted that closed end 118*a* and closed side ends 118*c* and 118*d*, may be stitched seams from first upper pocket 118 onto back side 106 of garment 100. Alternatively, first upper pocket 118 may be fixedly secured to back side 106 of garment 100 in a variety of ways, e.g., hot meld, and the like, so long as first upper pocket 118 is fixedly secured to garment 100.

Figure 8B:
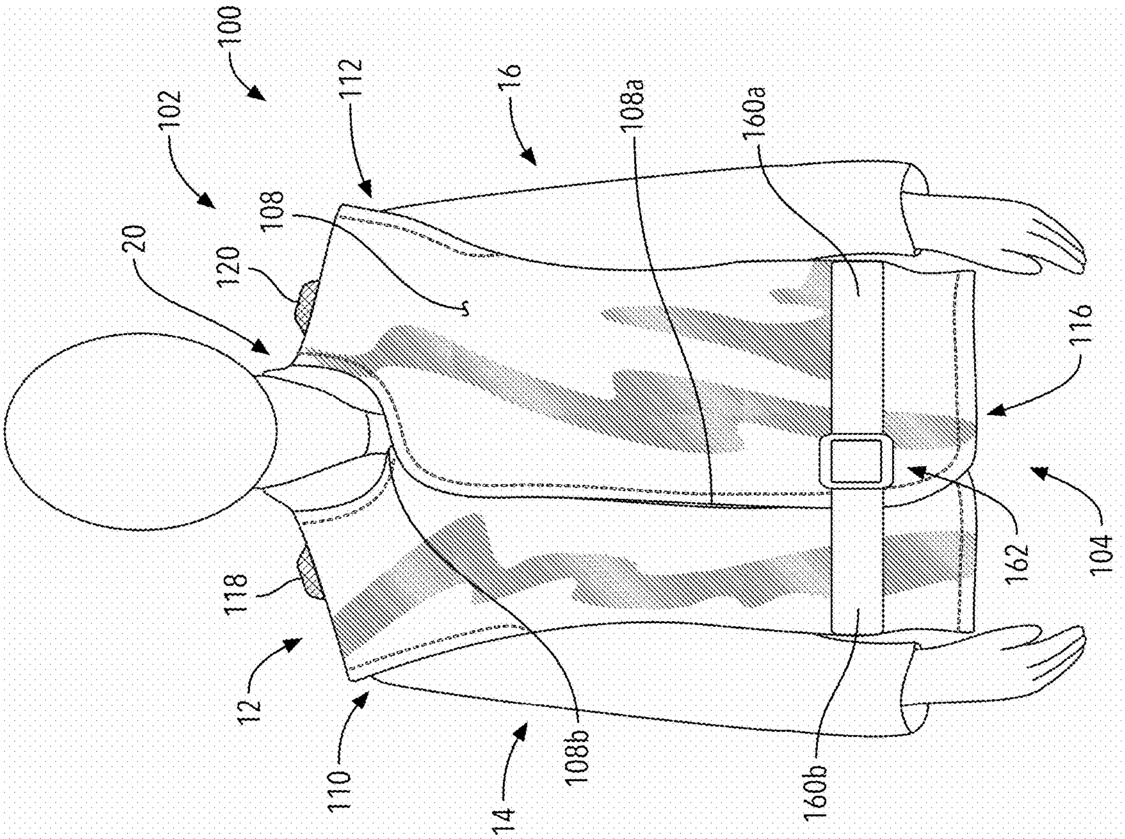
FIGS. 8A and 8B illustrate front and rear views of an alternative embodiment of the invention shown in FIG. 1.
Figure 8A:
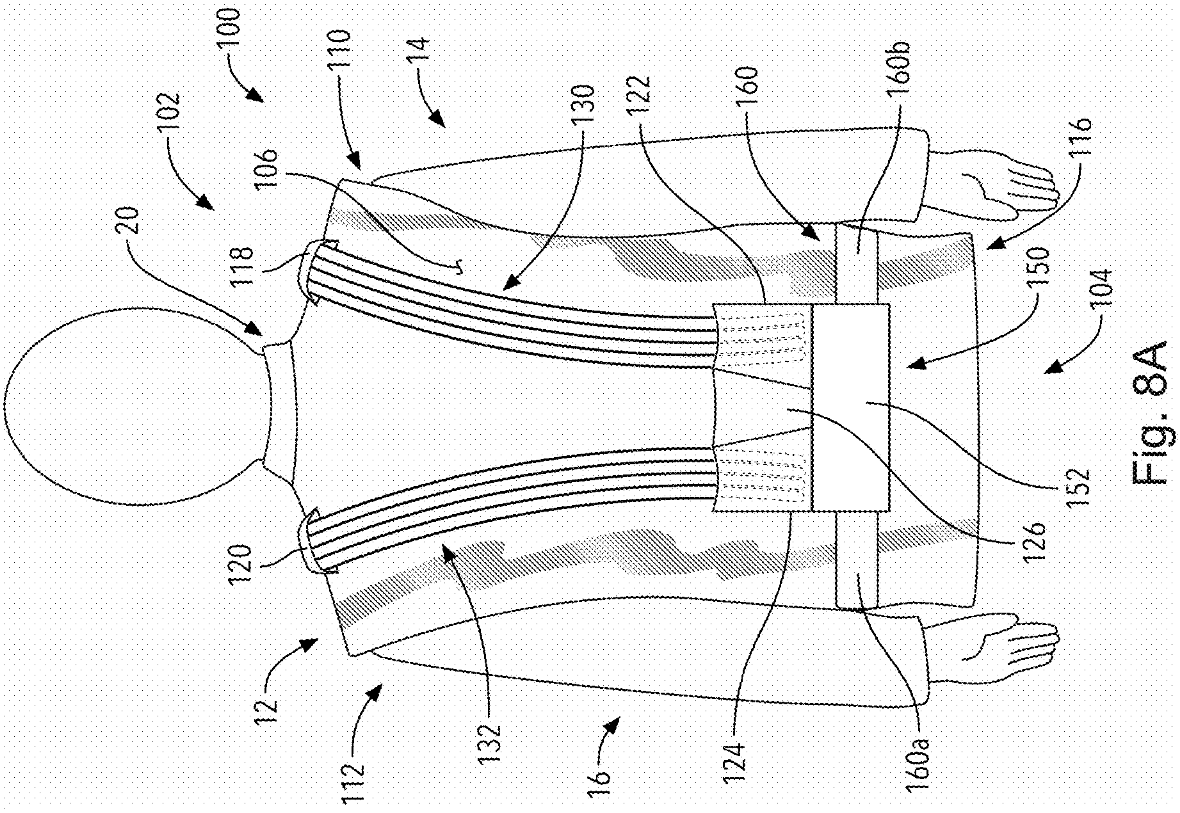

Adverting now to FIGS. 8A and 8B, which generally illustrate an alternative embodiment of garment 100, which includes support belt 160. In this alternative arrangement, lower pocket assembly 150, preferably lower section 152 thereof, has support belt 160 attached thereto and extending therefrom. Support belt 160 is arranged to wrap around the user, proximate waist end 104, such that support belt 160 is generally arranged on the user's lumbar back area. Support belt 160 may be comprised of first section 160*a* and second section 160*b*, which meet on front side 108, where fastener 162 may removably connect sections 160*a* and 160*b*. It should be noted that fastener 162 may not be necessary depending on the particular fastening configuration employed by sections 160*a* and 160*b* of support belt 160. In a non-limiting example, sections 160*a* and 160*b* may include hook and loop fasteners arranged thereon, allowing the respective sections to be removably connected at a desired tightness while also eliminating the need for fastener 162. As such, a hook and loop connection is only an exemplary illustration of one of many possible connection elements that may be employed to avoid the addition of fastener 162. Notwithstanding, fastener 162 could comprise a pair of mating buckles arranged at respective ends of sections 160*a* and 160*b*, which mating buckles allow for length adjustments of the respective sections to provide a desired tightness of support belt 160 once sections 160*a* and 160*b* are removably mated.

By including support belt 160 with lower pocket assembly 150, the weight transfer imparted by plurality of flexible rods 130 and 132 is further distributed to the lumbar section of the user's back, while support belt 160 also imparts additional support to the lumber section of the user's back. This combination further reduces the fatigue a user can experience, explained supra, from the weight of garment 100.

It should be noted that support belt 160 could be directly secured to at least a portion of one or more of back side 106 or front side 108, where pockets 122 and 124 may be fixedly secured on top of support belt 160, i.e., support belt 160 is sandwiched between a side of garment 100 and lower pocket assembly 150.

Figure 9:
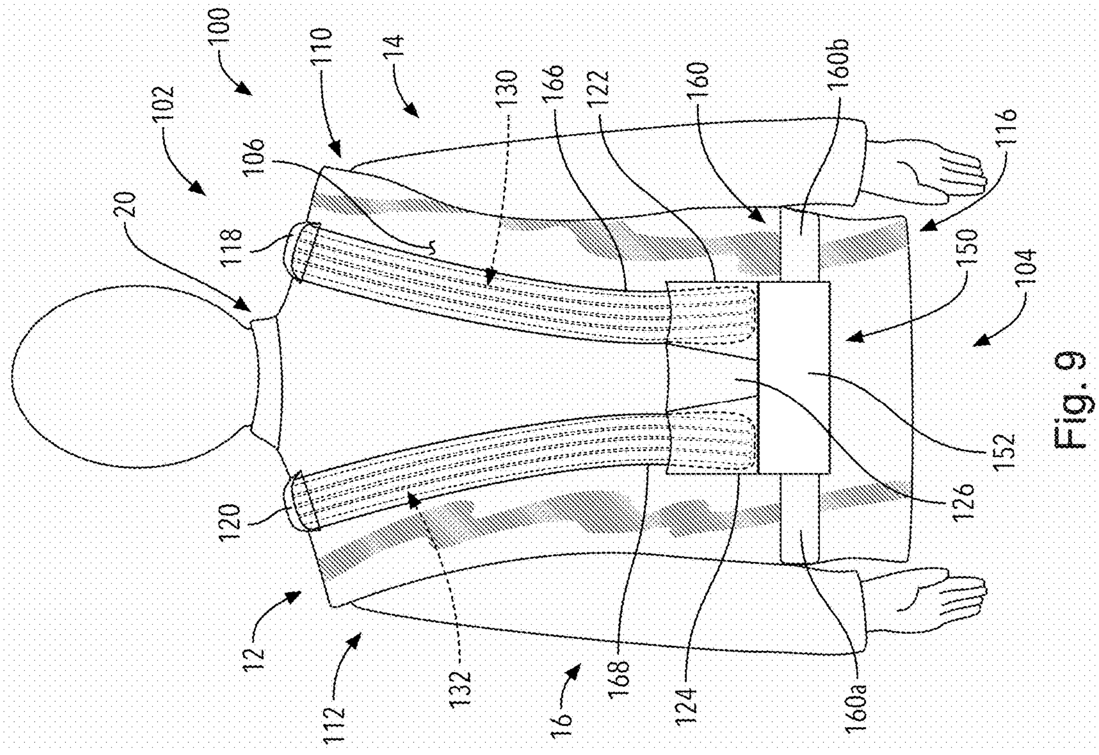
FIG. 9 illustrates the invention shown in FIG. 8A with protective sleeves for the plurality of rods.

As shown in FIG. 9, in another possible arrangement of garment 100, plurality of flexible rods 130 and 132 may be encased within a sleeve, individually, or collectively as a respective set, i.e., plurality of flexible rods 130 is encased within a first sleeve and plurality of flexible rods 132 is encased within a second sleeve. Sleeves 166 and 168 may be arranged to have plurality of flexible rods 130 arranged therein, where sleeve may have a closeable and known-in-the-art configuration to allow a various quantity of rods to be inserted therein, e.g., zipper, snaps, etc. Sleeves 166 and 168 are additional safety features for plurality of flexible rods 130 and 132, meaning that if one or more of the flexible rods snap, the respective pieces, halves, etc., are contained within the sleeve. This limits the potential for a shrapnel-like dispersion should one of the rods snap under force and avoid debris from being launched therefrom, protecting not only the user, but others who may be in proximity of the user.

Figure 10A:
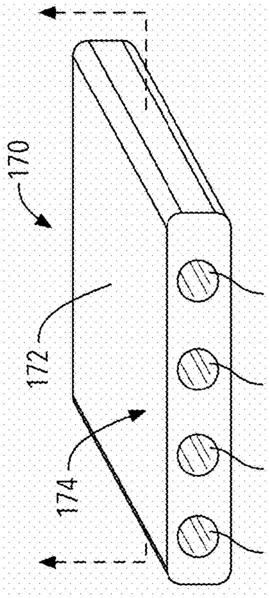
FIG. 10A illustrates a perspective view of an end cap of the invention shown in FIG. 1.
Figure 10B:
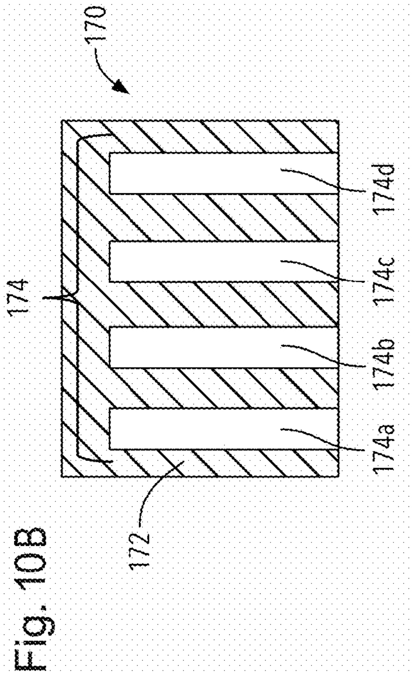
FIG. 10B illustrates a cross-sectional view taken generally along line 10B-10B in FIG. 10A; and, FIG. 11 illustrates a perspective view of a medial holder of the invention shown in FIG. 1.
Figure 11:
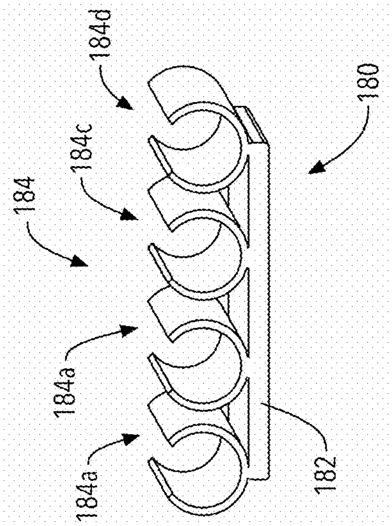

The following description should be taken in view of all of the aforementioned figures and FIGS. 10A-10B, and 11. FIGS. 10A and 10B illustrate a perspective and cross-sectional view of an end cap or end holder 170. End holder 170 generally includes body 172 having plurality of rod housings 174 arranged therein, e.g., compartments 174*a* through 174*d*. Preferably, each of plurality of rod housings 174 are a partial through-bore, having an open end and a closed end. The plurality of rod housings 174 are arranged to accept a respective end of each of rod of one of the plurality of flexible rods 130 and 132, e.g., compartment 174*a* may accept first end 134*a* or second end 134*b* of first flexible rod 134, compartment 174*b* may accept first end 136*a* or second end 136*b* of second flexible rod 136, compartment 174*c* may accept first end 138*a* or second end 138*b* of third flexible rod 138, and compartment 174*d* may accept first end 140*a* or second end 140*b* of fourth flexible rod 140. Therefore, in one possible configuration, there could be a pair of end holders for one plurality of flexible rods, where the end holders are arranged to be inserted within one or more of pockets 118, 120, 122, or 124, having the respective ends of the rods therein. This allows one plurality of flexible rods to be removed from a respective pair of upper and lower pockets as a set, thusly allowing different sets of rods, which may have greater or less weight reducing force, such that a single garment vest can be utilized by multiple users have different weight transferring needs. Moreover, the ends of the rods, which could be rough from cutting, are safely secured and surrounding within their respective compartments, further reducing potential injury. As such, compartments 174*a* through 174*d* may include gripping components therein, e.g., a taper which reduces in diameter in a direction away from the respective opening, gripping elements or tacky surface materials making the force to insert and/or remove greater, etc. It is also contemplated that the ends of each flexible rod may have a connector attached thereto and the compartments may have a respective mating connector arranged therein, allowing a mating interaction between the end of the flexible rod and the compartment of the end holder. It should be appreciated that the number of compartments within body 172 of end holder 170 is in a 1:1 ratio with the number of flexible rods for the respective plurality of flexible rods.

In another possible configuration, medial holder 180 may be frictionally and removably secured to one or more of plurality of flexible rods 130 and 132. Medial holder 180 includes body 182 having plurality of frictional clamps 184 comprised of clamps 184*a* through 184*d*, which have a C-shaped configuration. Each of plurality of frictional clamps 184 are arranged to frictionally "grab" and hold an outer surface of a flexible rod therein, thus keeping a portion of flexible rods, preferably other than the end thereof, e.g., a substantially middle portion, contained and in connection with the entire plurality of rods. Like end holder 170, It should be appreciated that the number of frictional clamps extending from within body 182 of medial holder 180 is in a 1:1 ratio with the number of flexible rods for the respective plurality of flexible rods.

EXAMPLES

It should be noted that the following description is exemplary and not intended to be limiting on the scope of the appending claims. Each of the flexible rods, discussed supra, may be approximately 0.16 inches in diameter and may have an approximate total length of 1.9 feet. With those exemplary dimensions, having a preferable total of eight (8) flexible rods, there is a weight reduction of at least 35% on a user's upper body, specifically the upper back, shoulders, and neck, with a sized SMALL vest, e.g., a vest length of approximately 22 inches measured from the highest point of the shoulder proximate the neck to proximate the waist and a frontal width of approximately 19 inches which is half of the user's chest circumference. As such, one having skill in the art can appreciate that the diameter and length of each flexible rod allows for variation of the total number of flexible rods. Additionally, length additions to each of flexible rods may be necessary to accommodate taller users who necessarily will have great vest length measurements to ensure the protective garment covers vital areas. Further, users having greater frontal widths, waist widths (measured similarly to frontal width), and/or hip widths (measured similarly to frontal width), may require additional rods to accommodate wider vest measurements, e.g., ten (10) total rods. Thus, one having skill in the art will appreciate that variations in one or more of a total number of flexible rods, an individual rod diameter, or an individual rod length, are contemplated within the scope of the appending claims.

It can be said that the distance between a pair of pockets, e.g., an upper pocket arranged on the shoulder section and a lower pocket, where both of the pockets are on the same side of the garment, have a length therebetween which is less than the length of a flexible rod inserted therein.

As such, the shown and described embodiments are merely exemplary and various alternatives, combinations, omissions, of specific components, or foreseeable alternative components, understood by one having ordinary skill in the art, described in the present disclosure or within the field of the present disclosure, are intended to fall within the scope of the appending claims.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMBERS

10 Person
12 Torso
14 Arm
16 Arm
18 Waist
20 Neck
22 Shoulder
24 Shoulder
100 Radiation protective garment with weight transferring apparatus
102 Neck end
104 Torso end
106 Back side/surface
108 Front side/surface
108*a* First end
108*b* Second end
110 First arm hole
112 Second arm hole
114 Neck/head hole
116 Waist hole
118 First upper pocket
118*a* Closed end
118*b* Open end
118*c* First closed side end
118*d* Second closed side end
118*e* Cavity
120 Second upper pocket
122 First lower pocket
122*a* Closed end
122*b* Open end
122*c* First closed side end
122*d* Second closed side end
124 Second lower pocket
124*a* Closed end
124*b* Open end
124*c* First closed side end
124*d* Second closed side end
126 Third lower pocket
126*a* Closed end
126*b* Open end
130 First plurality of flexible rods
132 Second plurality of flexible rods
134 First flexible rod
134*a* First end
134*b* Second end
136 Second flexible rod
136*a* First end

136*b* Second end
138 Third flexible rod
138*a* First end
138*b* Second end
140 Fourth flexible rod
140*a* First end
140*b* Second end
142 Fifth flexible rod
142*a* First end
142*b* Second end
144 Sixth flexible rod
144*a* First end
144*b* Second end
146 Seventh flexible rod
146*a* First end
146*b* Second end
148 Eighth flexible rod
148*a* First end
148*b* Second end
150 Lower pocket assembly
152 Lower section
160 Support belt
160*a* Section
160*b* Section
162 Fastener
170 End holder
172 Body
174 Plurality of rod housings
174*a* Compartment
174*b* Compartment
174*c* Compartment
174*c* Compartment
180 Medial holder
182 Body
184 Plurality of frictional clamps
184*a* Clamp
184*b* Clamp
184*c* Clamp
184*d* Clamp
CL Center line
F1 First force point
F2 Second force point
FP1 First flex point
FP2 Second flex point
5 S1 First space
S2 Second space

What is claimed is:

1. A radiation protective garment having a front surface, a back surface, a waist portion and a shoulder portion, said protective garment to be worn by a person having a waist and shoulders, comprising:

a first upper pocket arranged proximate said back surface and a first shoulder of said shoulder portion, said first upper pocket having a closed end facing said front surface;

a second upper pocket arranged proximate said back surface and a second shoulder of said shoulder portion, said second upper pocket having a closed end facing said front surface;

a first lower pocket arranged on said back surface and proximate said waist portion, said first lower pocket having a closed end facing said waist portion;

a second lower pocket arranged on said back surface and proximate said waist portion, said second lower pocket having a closed end facing said waist portion;

a first plurality of flexible rods supported by said first upper pocket and said first lower pocket; and, a second plurality of flexible rods supported by said second upper pocket and said second lower pocket.

2. The radiation protective garment recited in claim 1 further comprising a third lower pocket arranged between said first and second lower pockets on said back surface.

3. The radiation protective garment recited in claim 1, wherein said first plurality of flexible rods and said second plurality of flexible rods each comprise four flexible rods.

4. The radiation protective garment recited in claim 1, wherein each of said flexible rods of said first and second plurality of flexible rods are comprised of fiberglass.

5. The radiation protective garment recited in claim 1, wherein said first and second lower pockets are arranged proximate a center line of said back surface.

6. The radiation protective garment recited in claim 1, wherein said first plurality of flexible rods have a first flex point when supported by said first upper pocket and said first lower pocket; and, said second plurality of flexible rods have a second flex point when supported by said second upper pocket and said second lower pocket.

7. The radiation protective garment recited in claim 1, when worn by the person, wherein said shoulder portion is elevated above said shoulders of said person when said first plurality of flexible rods are supported by said first upper pocket and said first lower pocket; and, said second plurality of flexible rods are supported by said second upper pocket and said second lower pocket.

8. The radiation protective garment recited in claim 1, wherein each of said first plurality of flexible rods have a first end and a second end, and each of said second plurality of flexible rods have a first end and a second end.

9. The radiation protective garment recited in claim 8, wherein each end of each flexible rod is covered by a tip sleeve.

10. The radiation protective garment recited in claim 8, wherein:

said first ends of said first plurality of flexible rods are removably seated within said first upper pocket;

said first ends of said second plurality of flexible rods are removably seated within said second upper pocket;

said second ends of said first plurality of flexible rods are removably seated within said first lower pocket; and, said second ends of said second plurality of flexible rods are removably seated within said second lower pocket.

11. The radiation protective garment recited in claim 1 further comprising a support belt secured proximate said waist portion on said back surface, said support belt comprising a first section and a second section, said first and second sections adapted to be removably connected.

12. The radiation protective garment recited in claim 11, wherein said support belt includes a first end on said first section and a second end on said second section, a male buckle affixed to said first end, a female buckle affixed to said second end, said male buckle and said female buckle are operatively arranged to adjust a length of both sections.

13. The radiation protective garment recited in claim 11, wherein each of said sections of said support belt have a fastener and said fasteners are adapted to removably connect said sections of support belt together.

14. The radiation protective garment recited in claim 1 further comprising:

a first protective sleeve arranged to removably accept and hold said first plurality of flexible rods therein; and, a second protective sleeve arranged to removably accept and hold said second plurality of flexible rods therein.

15. A garment having a front surface, a back surface, a waist portion and a shoulder portion, said garment to be worn by a person having a waist and shoulders, comprising:

a first upper pocket arranged proximate said back surface and a first shoulder of said shoulder portion, said first upper pocket having a closed end facing said front surface;

a second upper pocket arranged proximate said back surface and a second shoulder of said shoulder portion, said second upper pocket having a closed end facing said front surface;

a first lower pocket arranged on said back surface and proximate said waist portion, said first lower pocket having a closed end facing said waist portion;

a second lower pocket arranged on said back surface and proximate said waist portion, said second lower pocket having a closed end facing said waist portion;

a first at least one flexible rod removably arranged within said first upper pocket and said first lower pocket; and, a second at least one flexible rod removably arranged within said second upper pocket and said second lower pocket, wherein when said rods are seated within the respective pockets they are flexed and extend away from said back surface.

16. The garment recited in claim 15 further comprising a support belt secured proximate said waist portion on said back surface, said support belt comprising a first section and a second section, said first and second sections adapted to be removably connected.

17. The garment recited in claim 15, wherein:

said first at least one flexible rod comprises a first plurality of flexible rods; and, said second at least one flexible rod comprises a second plurality of flexible rods.

18. The garment recited in claim 15, wherein:

said first plurality of flexible rods comprises at least four flexible rods; and, said second plurality of flexible rods comprises at least four flexible rods.

19. A radiation protective garment having a front surface, a back surface, a waist portion and a shoulder portion, the protective garment configured to be worn by a person having a waist and shoulders, comprising:

a first flexible rod and a second flexible rod, each having a length;

a pair of upper abutment structures, each integrated with a respective shoulder of the shoulder portion and each providing an upper abutment surface;

at least one lower abutment structure integrated with the back surface proximate the waist portion and providing at least one lower abutment surface; wherein:

the first flexible rod is constrained between a first of the upper abutment surfaces and the at least one lower abutment surface, and the second flexible rod is constrained between a second of the upper abutment surfaces and the at least one lower abutment surface; and, the length of each of said first and second flexible rods is greater than a linear distance between its respective upper and lower abutment surfaces, such that each rod is maintained in a flexed state.

* * * * *